United States Patent [19]

Van Bramer et al.

[11] Patent Number: 5,345,013
[45] Date of Patent: Sep. 6, 1994

[54] SAFE HANDLING OF TETRAFLUOROETHYLENE

[75] Inventors: David J. Van Bramer, Belpre, Ohio; Mark B. Shiflett, Newark; Akimichi Yokozeki, Wilmington, both of Del.

[73] Assignee: E. I. du Pont de Nemours and Company, Wilmington, Del.

[21] Appl. No.: 74,635

[22] Filed: Jun. 10, 1993

[51] Int. Cl.$^5$ .................. C07C 17/42; C07C 21/185
[52] U.S. Cl. .................................. 570/102; 570/103
[58] Field of Search .................... 570/102, 117, 103

[56] References Cited

U.S. PATENT DOCUMENTS

| | | | |
|---|---|---|---|
| 2,407,405 | 9/1946 | Dietrich et al. | 570/103 |
| 2,407,419 | 9/1946 | Hanford | 570/103 |
| 2,737,533 | 3/1956 | Marks et al. | 570/103 |
| 3,873,630 | 3/1975 | West | 260/653.3 |
| 4,365,102 | 12/1982 | Couture et al. | 157/163 |

FOREIGN PATENT DOCUMENTS

| | | |
|---|---|---|
| 4539082 | 12/1970 | Japan . |
| 5748096 | 10/1982 | Japan . |

OTHER PUBLICATIONS

Kobayashi and Endo, Repressing Effects of Diluent Gases on the Disproprortionation Reaction of Tetrafluoroethylene (1988).

*Primary Examiner*—Joseph E. Evans
*Attorney, Agent, or Firm*—Edwin Tocker

[57] ABSTRACT

Tetrafluoroethylene is made safe (non-explosive) to handle by forming a liquid solution of tetrafluoroethylene and carbon dioxide, one in the other, in a pressurized container.

17 Claims, No Drawings

SAFE HANDLING OF TETRAFLUOROETHYLENE

BACKGROUND OF THE INVENTION

This invention relates to the safe handling of tetrafluoroethylene under confinement.

Tetrafluoroethylene (TFE) is a gas at ambient temperature (20° C.), but can be liquified by sufficient pressurization in a container, to provide a relatively large quantity of the tetrafluoroethylene within the container. For economic or space-saving reasons, it is desireable to store or transport TFE as a liquid because a greater amount of TFE can be stored in a given space.

TFE is flammable when mixed with air and exposed to such conditions as atmospheric pressure and contact with a hot surface at a temperature of about 240° C. The greater danger presented by TFE, however, is the explosivity of TFE gas vaporizing from TFE liquid contained under pressure. This explosivity results from the decomposition of TFE to $CF_4$ and C. This explosive decomposition can result from exposure of the TFE vapor to high temperatures. Also, the susceptability to explosion increases with increasing TFE pressure. Oxygen can cause autopolymerization of TFE, which can in turn cause sufficient localized heating within the container to cause the TFE vapor above the liquid within the container to explode. The explosivity of TFE may not depend on the presence of air, however, since air will normally be excluded (purged) from the container of liquid TFE. Even in the absence of air, exposure of the TFE vapor within the container to a spark, such as caused by discharge of static electricity, a hot metal surface, such caused by metal surfaces rubbing together, or an external fire can cause the TFE vapor to explode. Thus, for example, a saturated TFE vapor can explode at temperatures of $-16°$ C. or greater when under a pressure of at least 150 psia (1032 KPa), while an unsaturated TFE vapor can explode at 25° C. and 115 psia (790 KPa).

Heretofore, the problem of TFE explosivity during transportation has been solved by adding HCl to the liquid tetrafluoroethylene within the pressurized container, the proportion of TFE to HCl being about 33 mol % TFE and 67 mol % of HCl. This mixture forms an azeotrope, so as tetrafluoroethylene vaporizes, so does HCl in about the same proportion. The presence of HCl with the TFE in the vapor state renders the TFE non-ignitable, and therefore non-explosive, in the absence of air. While this solution solves the problem of the explosion hazard of the tetrafluoroethylene, this solution has both the problem of disposal of the large amount of HCl present with the tetrafluoroethylene, when the tetrafluoroethylene is to be used, e.g. in polymerization to polytetrafluoroethylene and other polymers, as well as the HCl toxicity problem in the event of an accidental release. The disposal problem is also true for the use of trifluorotrichloroethane or a perfluoroalkane, as disclosed in Japanese Kokai 45-39082 (Dec. 9, 1970) and 57-48096 (Oct. 14, 1982), respectively, in admixture with liquid tetrafluoroethylene for safe storage, unless they are specifically desired as components or carrier solvents for the specific use.

U.S. Pat. No. 4,365,102 discloses the heating of gaseous mixtures of TFE and $CO_2$ at temperatures of 950° to 1500° C. in order to make $CF_4$ and $C_2F_6$, with the $CO_2$ being disclosed to act as a diluent for the TFE to reduce the chance of explosion due to the decomposition of TFE (at $CO_2$ molecular concentrations greater than 20 mol % $CO_2$) at the reaction temperature and to act endothermically to moderate the temperature rise coming from the heat of the chemical reaction. U.S. Pat. No. 3,873,630 discloses pyrolysis of a TFE/$CO_2$ (8 to 70 mol % $CO_2$) gaseous mixture at 700° to 900° C. and essentially atmospheric pressure to obtain hexafluoropropylene. It also discloses that >8 mol % $CO_2$ is needed in the gaseous feed to the pyrolysis furnace to render TFE non-explosive at essentially one atmosphere pressure, and that >60 mol % $CO_2$ is needed in the feed to render the TFE/$CO_2$ feed mixture non-flammable in case of leakage to the atmosphere.

Asahi Garasu Kenkyu Hokoku 38 no.1:115-22 (1988) entitled "Repressing Effects of Diluent Gases on the Disproportionation Reaction of Tetrafluoroethylene" discloses bringing together TFE with various diluent gases, including inert gases, notably $N_2$ and $CO_2$, for a short period of time at initial pressures of 157 to 228 psia (1080–1569 KPa) and undisclosed temperature and then igniting the resultant mixture, with the result being explosion of the mixtures at lower concentrations of diluent gas (15 mol % $CO_2$) but not explosion at higher concentration (18 mol % $CO_2$).

SUMMARY OF THE INVENTION

The present invention provides single-phase, liquid mixtures of tetrafluoroethylene and carbon dioxide. The TFE and $CO_2$ are completely miscible with one another over all the entire range of possible compositions.

The present invention also provides for the confinement of the liquid mixture under pressure. This confinement can simply be referred to as a container, such as for storage or transportation. The $CO_2$ mixed with the TFE can be subsequently used as a polymerization medium for the TFE as described in U.S. Pat. No. 4,861,845 or as a diluent/heat sink in chemical reactions involving the TFE. The utility of the TFE/$CO_2$ liquid mixture as a mode for safe handling of TFE, such as for storage and transportation of the TFE will be the utility described in detail herein. In that utility, when pure TFE needs to be recovered from the container, the $CO_2$ can easily be separated from the TFE via conventional scrubbing technology or membrane separation technology or the combination thereof, and returned to the atmosphere, i.e., there is no waste disposal problem.

DETAILED DESCRIPTION $CO_2$ sublimes at $-78.5°$ C. and has a triple point at $-56.6°$C. while tetrafluoroethylene boils at $-75.6°$ C. Under conditions where $CO_2$ and TFE are liquid, surprisingly, liquid $CO_2$ is miscible with TFE in the liquid state over the entire range of compositions, e.g. 1 to 99 mol % $CO_2$ and 99 to 1 mol % TFE.

In most applications of storage or transportation of the liquid TFE/$CO_2$ mixture in a container, the container will become internally pressurized by vaporizing TFE and $CO_2$ from the liquid mixture within the usual temperature range to which the container may be exposed, e.g. $-50°$ to $+55°$ C. The presence of the $CO_2$ in the liquid can provide an effective amount of $CO_2$ in the vapor to prevent the TFE from exploding when exposed to the hazards hereinbefore described. Unexpectedly, the TFE and $CO_2$ vaporize from the TFE/$CO_2$ liquid mixture at nearly the same rate, resulting in significantly less change in the liquid composition, and therefore in the vapor composition, than would be expected.

This means that in case of vaporization of the liquid from the container, i.e., leakage of the vapor from the container, as might occur from an accident during transportation, the $CO_2$ will continuously vaporize with the TFE from the liquid mixture, so as to be present with the TFE vapor to suppress its explosivity. The reason this is unexpected is that $CO_2$ is about two times more volatile than TFE, e.g. 2:1 at $-35°$ C., and 1.9:1 at 15° C. If the components of the TFE/$CO_2$ liquid mixture volatilized at the rate of their respective individual volatilities, the more volatile $CO_2$ would be expected to vaporize first and leave behind a TFE-rich liquid, the vapor from which would be susceptible to explosion. Instead, the $CO_2$ concentration in the vapor remains substantially constant as the liquid vaporizes, which is characteristic of an azeotrope, except that this phenomenon occurs over the entire range of TFE/$CO_2$ liquid compositions and temperature and pressure ranges at which the liquid mixture would be handled.

The partial pressures of the TFE and $CO_2$ vapors, although quite different from one another, within the container contribute to the total vapor pressure within the container. The substantial constancy of the vapor composition as more and more of the liquid mixture vaporizes, as will occur when the container leaks, can conveniently be determined by measurement of the vapor pressure within the container, as indicating the substantial constancy of the composition of the vapor. The unexpected azeotrope-like behavior of the TFE/$CO_2$ liquid mixture of the present invention can be characterized by only small changes in vapor pressure occurring within the container as the liquid mixture vaporizes from the container. For example, upon vaporization of the liquid mixture, the change in vapor pressure can be less than 10% of the starting vapor pressure (prior to the leak) after 50 wt % of the starting liquid has vaporized, and preferably even after 80 wt % of the starting liquid has vaporized.

The present invention can be practiced by pressurizing $CO_2$ and TFE to form liquids and then mixing the TFE liquid into the $CO_2$ liquid in the proportion desired. Preferably, the $CO_2$ is liquified and then the TFE is condensed in this liquid to form the mixture. In another embodiment, pressurized TFE and $CO_2$ gases can be mixed together, followed by temperature reduction to form a liquid mixture without any need for stirring. Once the liquid mixture is formed, it can then be added to a container which had been previously purged of air (oxygen). The addition of the liquid mixture to the container will usually be such as to underfill the container at the filling temperature of the liquid mixture, e.g. at $-50°$ C. in order to limit the internal pressure developed in the event temperature should exceed the critical temperature. The critical temperatures of $CO_2$ and TFE are 31° C. and 32.8° C., respectively. When the liquid mixture is first added to the container, the vapor space remaining in the container quickly becomes saturated with TFE and $CO_2$ vapor from the liquid. Any increase of the liquid mixture temperature within the container drives more and more liquid into the vapor state within the container to increase the pressurization thereof. In transportation, the maximum ambient temperature to which the container might be exposed is about 55° C. on a worldwide basis, but in most locales, a maximum of about 46° C.

The amount of underfilling of the container will depend on the container, e.g. whether refrigerated or unrefrigerated, and whether the container is for local storage or transportation. On the one hand, federal regulations may dictate substantial underfilling of containers used for transportation so as to leave substantial vapor space within the container. This would minimize the buildup of pressure in case the liquid heats up above its critical temperature during transportation. On the other hand, greater latitude is available for filling refrigerated containers for storage only. Generally, the pressurization of the vapor within the container over the temperature range of $-50°$ to $+55°$ C., will be from 115 to 4015 psia (790 to 27677 KPa) and the filling of the container with liquid mixture will be within the range of 50 to 90% of the container water capacity. The vol % filling of the container with liquid mixture can be such that the maximum pressure within the container and within the temperature range $-50°$ to $+55°$ C. will be 1615 psia (11131 KPa) or less.

It has been determined that at least 30 mol % $CO_2$ in the vapor space of the container will prevent the TFE from exploding over the temperature range of $-50°$ to $+55°$ C. and at pressures up to at least 1615 psi (11131 KPa). The same concentration in the liquid will provide this vapor concentration even after 80 wt % of the TFE/$CO_2$ liquid mixture in the container has been allowed to vaporize from the container, including at temperatures exceeding the critical temperature of the liquid mixture. Thus, a preferred liquid composition is 30–99 mol % $CO_2$ and 1–70 mol % TFE, to total 100 mol %. This protects the TFE/$CO_2$ vapor mixture even at temperatures at and above the critical temperature of the liquid mixture, at least up to 55° C., and even at pressures of 115 psia (790 KPa) and above.

Smaller proportions of $CO_2$ in the liquid can also be used in applications involving lesser explosion hazard, e.g. milder ignition possibility or storage or transportation at a lower temperature or storage, wherein the exposure to an accident which might rupture the container does not exist. Ten mol % $CO_2$ in the liquid can provide sufficient $CO_2$ in the vapor space (about 15 mol %) to prevent explosion at temperatures up to $+10°$ C. within a closed system. To extend this protection to a closed system at a temperature up to $+20°$ C., then the liquid should contain 15 mol % $CO_2$. This provides the vapor space with at least 20 mol % $CO_2$ at temperatures up to $+20°$ C. The liquid compositions described in this paragraph are thus, 10–99 mol % $CO_2$ and 1–90 mol % TFE; 15–99 mol % $CO_2$ and 1–85 mol % TFE; 20–99 mol % $CO_2$ and 1–80 mol % TFE, to total 100 mol %.

The amount of $CO_2$ needed to prevent explosion is intended to refer to the explosion condition where the TFE/$CO_2$ vapor is exposed to an electrical resistance wire which upon passage of sufficient current through the wire, causes the wire to glow and upon reaching 1350° C. to fuse (melt), breaking the electrical circuit and thereby discontinuing the exposure of the vapor to this source of intense heating. The commonly available Nichrome ® resistance wire has the property of reaching 1350° C. and fusing at this temperature when subjected to sufficient electric current. The time of the exposure to this ignition test is unimportant, but sometimes the current in the wire is increased over a period of several seconds, to detect whether explosion occurs prior to reaching the fusion temperature. For a quicker test, the time period may only be 1 second to reach fusion of the wire to see whether explosion occurs at the highest temperature of the test. The temperature of the vapor at which the test is conducted can be any temperature within the range stated for particular TFE/$CO_2$ mixtures. The heating up of the wire is so quick that the bulk temperature of the vapor undergoes no appreciable temperature increase (unless the vapor were to explode) during the ignition test. A preferred temperature of the vapor for the ignition test is 25° C. as being the temperature that shipped or stored liquid TFE/CO$_2$ mixture might be expected to reach most often. This is the temperature condition used in Example 7, while higher temperatures were used for Example 8. Non-explosion at the higher temperatures in Example 8 means that the mixtures tested in that Example would not explode at 25° C. either. With respect to pressure, the higher the pressure of the vapor, the greater the tendency to explode because of the greater presence of TFE molecules in the vicinity of the ignition source. Thus a pressure will be chosen for the ignition test that would cause explosion at the test condition if CO$_2$ were not present. Example 8 shows non-explosion at the extremely high pressure of 1664 psia (11469 KPa).

At −35° C. and at 96 mol % CO$_2$ concentration in the liquid a true azeotrope with TFE is formed.

The higher the proportion of CO$_2$ in the liquid, the greater will also be the resistance of the TFE vapor to burn when exposed to the air and conditions of flammability upon leakage from the container. The protective association of the CO$_2$ with the TFE within the vapor space continues with the escape of the mixed vapor into the air. For flammability suppression, preferably, the liquid contains at least 60 mol % of CO$_2$, which provides at least 60 mol % CO$_2$ in the vapor even after up to 80 wt % of the liquid has vaporized from the container.

The container which confines the TFE and CO$_2$ can have a wide variety of forms and functions. For example, the container can simply be a pipe or a storage tank or can be in such transportable forms as tank trucks, cylinders or pipes for transportation, such as by truck, ship (barge) or railway tank car. The container can also be chemical reaction or processing equipment. The period of storage can be a short period, e.g. at least one hour, or can be for a long period, e.g. weeks or months. The containers require no special construction or materials of construction other than being capable of containing the liquid mixture under the internal pressures that might be encountered. One skilled in the art will also recognize that the precautions heretofore practiced in safe handling of TFE, e.g. for storage and transportation, should also be incorporated into the practice of the present invention.

EXAMPLES

EXAMPLE 1

In this experiment, the mole fraction of CO$_2$ in vapor arising from a range of TFE/CO$_2$ miscible liquid mixtures was determined.

To a phase-equilibrium cell (the container), consisting of a glass cylinder 2" (5.1 cm) in diameter by 6" (15.2 cm) clamped between stainless steel flanges, known amounts of high purity TFE (>99.8%) and CO$_2$ (>99.99%) liquids were displaced from their respective temperature controlled cylinders by mercury. The cell was agitated via a magnetically coupled turbine-type agitator and its temperature was controlled via total immersion in an oil bath.

Pressures were measured by balancing a differential pressure transducer with nitrogen, whose pressure was measured on a digital pressure gauge. Liquid compositions were corrected for the amount calculated to be in the vapor phase. Vapor compositions were calculated by correlating the liquid composition and cell pressure data to the Wilson equation for activity coefficients and the Peng-Robinson equation-of-state for the compressibility factors and the fugacity coefficients. Selected vapor samples were also taken from the cell and analyzed by gas chromatography to cross-check the calculated results.

The system TFE/CO$_2$ was found to be fully miscible over the entire range measured by both visual observation of the liquid/gas interface and by detecting no regions of constant pressure as a function of composition. The absence of any region of constant pressure meant the absence of two liquid phases, indicating the full miscibility of the TFE and CO$_2$ one with the other.

Results from measurements at +15° C. were:

TABLE 1

| Mol Fraction CO$_2$ in Liquid in Container | Vapor Pressure (KPa)[1] | Mole Fraction CO$_2$ in Vapor | |
|---|---|---|---|
| | | Calc. | Meas. |
| .898 | 4989 | .909 | .911 |
| .789 | 4823 | .820 | — |
| .693 | 4643 | .736 | — |
| .556 | 4319 | .620 | — |
| .494 | 4153 | .566 | .575 |
| .406 | 3903 | .486 | — |
| .297 | 3596 | .379 | — |
| .196 | 3272 | .269 | — |
| .098 | 2952 | .146 | — |
| .038 | 2749 | .060 | .038 |

[1]Data in this and other Tables herein obtained in psia; converted to KPa by multiplying psia × 6.895 and rounding off answer.

EXAMPLE 2

The results from conducting a similar experiment as Example 1, but at −35° C., show that the TFE and CO$_2$ liquids were also fully miscible at this temperature, but also surprisingly, an azeotrope at about 96 mol % CO$_2$ was formed. The vapor pressure at which the azeotrope exists at −35° C. is about 1205 KPa.

TABLE 2

| Mol Fraction CO$_2$ in Liquid in Container | Vapor Pressure (KPa) | Mole Fraction CO$_2$ in Vapor | |
|---|---|---|---|
| | | Calc. | Meas. |
| .979 | 1203 | .978 | .980 |
| .950 | 1204 | .950 | — |
| .898 | 1201 | .908 | — |
| .748 | 1164 | .808 | — |
| .670 | 1136 | .761 | — |
| .602 | 1112 | .719 | — |
| .487 | 1043 | .642 | .638 |
| .385 | 975 | .563 | — |
| .300 | 907 | .485 | — |
| .198 | 816 | .367 | — |
| .099 | 717 | .215 | — |
| .029 | 640 | .071 | .070 |

EXAMPLE 3

In equipment identical to that in Example 1, 238.8 cc of a 34 mol % CO$_2$/66 mol % TFE liquid mixture was added to the cell and equilibrated to +25° C. Vapor was then slowly vented from the cell, while maintaining isothermal conditions, and collected in a 1-gallon (0.0038 m$^3$) cylinder until 10% of the original liquid volume had disappeared visually, and confirmed by a cathetometer. The amount of material vented was determined from the known volume of the 1-gallon (0.0038 m$^3$) cylinder and the temperature and pressure of the gas in the cylinder. This was repeated, in 10% intervals, until all the liquid had visually disappeared and a change in the slope of the pressure reduction curve indicated that there was no more liquid left in the cell.

TABLE 3

| Grams of TFE + $CO_2$ Vented | Volume % Liquid Removed | Weight % Liquid Removed | Vapor Pressure (KPa) | % Pressure Reduction |
|---|---|---|---|---|
| 0 | 0 | 0 | 4631 | 0 |
| 8.82 | 9.5 | 8.8 | 4613 | 0.4 |
| 18.07 | 20.0 | 18.1 | 4596 | 0.7 |
| 27.05 | 29.4 | 27.1 | 4583 | 1.0 |
| 37.93 | 40.7 | 38.0 | 4560 | 1.5 |
| 47.65 | 50.8 | 47.8 | 4529 | 2.2 |
| 58.09 | 61.2 | 58.2 | 4505 | 2.7 |
| 99.74 | 99.0 | 99.0 | 4349 | 6.1 |
| 110.02 | 100 | 100 | 4211 | 9.1 |

The relative constant vapor pressure (low % pressure reduction) in the cell throughout the time of venting shows the relative constant proportion of $CO_2$ and TFE in the remaining saturated vapor.

EXAMPLE 4

Because of high pressures in the series of tests under this Example, the cell was changed for this series of tests to a metal cell. Other than not being able to detect the volume change visually, the test protocol was similar to that in Example 3. Reduction in liquid volume was calculated based on the known amount of TFE and $CO_2$ in the cell, the amount vented, and previously determined vapor and liquid densities. At 25° C., the following results were obtained:

TABLE 4a

Liquid Composition = 68.9 mol % $CO_2$

| Grams of TFE + $CO_2$ Vented | Volume % Liquid Removed | Weight % Liquid Removed | Vapor Pressure (KPa) | % Pressure Reduction |
|---|---|---|---|---|
| 0 | 0 | 0 | 5881 | 0 |
| 34.95 | 45.1 | 44.1 | 5837 | 0.8 |
| 42.02 | 54.2 | 53.0 | 5830 | 0.9 |
| 63.03 | 80.8 | 79.5 | 5796 | 1.5 |
| 69.96 | 89.2 | 88.3 | 5766 | 2.0 |
| 76.96 | 97.1 | 97.1 | 5713 | 2.9 |
| 90.98 | 100 | 100 | 5519 | 6.2 |

TABLE 4b

Liquid Composition = 94.6 mol % $CO_2$

| Grams of TFE + $CO_2$ Vented | Volume % Liquid Removed | Weight % Liquid Removed | Vapor Pressure (KPa) | % Pressure Reduction |
|---|---|---|---|---|
| 0 | 0 | 0 | 6373 | 0 |
| 46.46 | 44.5 | 44.3 | 6363 | 0.2 |
| 57.85 | 55.4 | 55.2 | 6363 | 0.2 |
| 80.83 | 77.4 | 77.1 | 6359 | 0.2 |
| 92.43 | 88.5 | 88.1 | 6354 | 0.3 |

TABLE 4b-continued

Liquid Composition = 94.6 mol % $CO_2$

| Grams of TFE + $CO_2$ Vented | Volume % Liquid Removed | Weight % Liquid Removed | Vapor Pressure (KPa) | % Pressure Reduction |
|---|---|---|---|---|
| 115.85 | 100 | 100 | 6050 | 5.1 |

The $CO_2$ content of the TFE/$CO_2$ vapor was fairly constant in both experiments 4a and 4b as indicated by the relatively constant vapor pressure (low % pressure reduction). Examples 3 and 4 show that at +25° C. and pressures of about 4000 to 6500 KPa, compositions of about 30 to 99 mol % $CO_2$ and 70 to 1 mol % TFE are azeotrope-like in exhibiting reduction in vapor pressure of less than 10% when up to 50 wt % of the liquid is vaporized and even when up to 80 wt % of the liquid is vaporized.

EXAMPLE 5

The data from Examples 1 and 2, as well as data taken at a temperature of −10° C., were correlated to the Soave-Redlich-Kwong equation-of-state and analyzed for the prediction of azeotropes other than found in Example 2. From this analysis, the azeotrope at −35° C. found at about 96 mol % $CO_2$ in Example 2 was predicted to be at 93 mol % $CO_2$. This is an excellent correlation between observed and calculated results. As shown in Table 5, the azeotrope composition is predicted to shift in the direction of TFE-richer, as a function of lower temperatures.

TABLE 5

| Temperature (°C.) | Mole Fraction $CO_2$ in Liquid | Mole Fraction $CO_2$ in Vapor | Vapor Press. (KPa) | Pred. Azeo. mol % $CO_2$ |
|---|---|---|---|---|
| −35 | 1.000 | 1.000 | 1196 | ~93 |
|  | .950 | .947 | 1205 |  |
|  | .900 | .906 | 1205 |  |
|  | .850 | .871 | 1198 |  |
| −45 | 1.000 | 1.000 | 827 | ~92 |
|  | .950 | .945 | 836 |  |
|  | .900 | .903 | 838 |  |
|  | .850 | .869 | 835 |  |
| −55 | 1.000 | 1.000 | 552 | ~90 |
|  | .950 | .941 | 560 |  |
|  | .900 | .899 | 563 |  |
|  | .850 | .865 | 562 |  |

EXAMPLE 6

The model developed in Example 5 was used to predict the vaporization behavior of the TFE/$CO_2$ liquid system for additional compositions at different (lower) temperatures. The data shown in Table 6a shows some of the compositions expected to contain at least 60 mol % $CO_2$ in the vapor space, even after 80 wt % of the initial liquid has been vaporized.

TABLE 6a

| Mol %[1] $CO_2$ in Liquid | Liquid Vaporized | | | | | | | |
|---|---|---|---|---|---|---|---|---|
| | 0 wt % | | 50 wt % | | | 80 wt % | | |
| | Press. (KPa) | M % $CO_2$ Vapor | Press. (KPa) | % Press. Change | M % $CO_2$ Vapor | Press. (KPa) | % Press. Change | M % $CO_2$ Vapor |
| Saturated Temperature = −50° C. | | | | | | | | |
| 84.1 | 687 | 86.2 | 686 | 0.2 | 85.4 | 685 | 0.4 | 84.7 |
| 69.4 | 666 | 78.1 | 652 | 2.1 | 74.9 | 638 | 4.1 | 72.0 |
| 61.2 | 645 | 73.2 | 618 | 4.2 | 68.1 | 593 | 8.0 | 63.6 |
| Saturated Temperature = +20° C. | | | | | | | | |
| 84.1 | 5571 | 85.5 | 5557 | 0.3 | 84.9 | 5550 | 0.4 | 84.4 |
| 69.4 | 5233 | 72.5 | 5185 | 0.9 | 71.1 | 5151 | 1.6 | 70.1 |

TABLE 6a-continued

| Mol %[1] | Liquid Vaporized | | | | | | | |
|---|---|---|---|---|---|---|---|---|
| | 0 wt % | | 50 wt % | | | 80 wt % | | |
| $CO_2$ in Liquid | Press. (KPa) | M % $CO_2$ Vapor | Press. (KPa) | % Press. Change | M % $CO_2$ Vapor | Press. (KPa) | % Press. Change | M % $CO_2$ Vapor |
| 61.2 | 4964 | 64.4 | 4895 | 1.4 | 62.4 | 4847 | 2.4 | 61.1 |

[1] 84.1, 69.4, and 61.2 mol % $CO_2$ correspond to 70, 50, and 40 wt % $CO_2$, respectively.

The model in Example 6 above is used to predict behavior that results in $CO_2$ vapor concentrations exceeding 20 mol % after 80 wt % of the initial liquid has been vaporized.

TABLE 6b

| Mol %[1] | Liquid Vaporized | | | | | | | |
|---|---|---|---|---|---|---|---|---|
| | 0 wt % | | 50 wt % | | | 80 wt % | | |
| $CO_2$ in Liquid | Press. (KPa) | M % $CO_2$ Vapor | Press. (KPa) | % Press. Change | M % $CO_2$ Vapor | Press. (KPa) | % Press. Change | M % $CO_2$ Vapor |
| Saturated Temperature = −50° C. | | | | | | | | |
| 20.2 | 473 | 40.2 | 423 | 10.8 | 27.6 | 405 | 14.6 | 22.7 |
| 20.2 | 473 | 40.2 | 423 | 10.8 | 27.6 | 405 | 14.6 | 22.7 |
| 36.2 | 558 | 57.1 | 501 | 10.3 | 46.0 | 472 | 15.3 | 39.8 |
| 49.3 | 611 | 66.7 | 568 | 7.2 | 58.8 | 536 | 12.2 | 53.2 |
| Saturated Temperature = +20° C. | | | | | | | | |
| 20.2 | 3628 | 26.0 | 3530 | 2.7 | 22.9 | 3482 | 4.0 | 21.2 |
| 36.2 | 4185 | 42.5 | 4068 | 2.8 | 39.3 | 4006 | 4.3 | 37.5 |
| 49.3 | 4620 | 54.7 | 4523 | 2.1 | 52.1 | 4461 | 3.4 | 50.5 |

[1] 20.2, 36.2, and 49.3 mol % $CO_2$ correspond to 10, 20, and 30 wt % $CO_2$, respectively.

The data on mol % concentration of $CO_2$ in the vapor in Tables 6a and b show the presence of certain minimum amounts of $CO_2$ being present in the vapor over a wide range of temperatures and liquid compositions even after most of the liquid composition would have been vented as a vapor from its original container. For example, at −50° C., 78.1 mol % $CO_2$ in the vapor arising from 69.4 mol % $CO_2$ in the TFE/$CO_2$ liquid composition diminishes only to 72 mol % after venting of 80% of the composition (Table 6a). At +20° C., the same composition exhibits a vapor pressure reduction of only 1.6% (5233-5151 KPa) (Table 6a). At the highest TFE concentration of 79.8 mol % either at −50° C. or +20° C., the mol % $CO_2$ in the vapor still exceeds 20 mol % after the venting of 80 wt % of the liquid (Table 6b).

EXAMPLE 7

Ignition Test: Series #1

Tetrafluoroethylene (TFE) was charged to a pressure of 165 psia (1138 KPa) to an evacuated 250 cc Parr bomb at room temperature (20 C.). This pressure and temperature combination is known to be sufficient to result in TFE decomposition (ignition) in the presence of a red-hot (1350° C.) No. 28 Nichrome ignitor wire, 2 inches in length, placed in the center of the bomb. Next, carbon dioxide ($CO_2$) was added to the Parr bomb to the pressure level desired and power was applied to the ignitor wire. Ignition of the TFE/$CO_2$ system was detected mainly by pressure rise on a gauge attached to the bomb. This system (test) simulates the vapor mixture present in the container of liquid TFE/$CO_2$ mixture at any particular time in the container and at particular temperature within the range −50 to +55 C. at which the contents of the bomb (container) are at when exposed to the explosion hazard, whether the vapor mixture is confined within the container or is vaporizing (escaping) from the container.

In one experiment, at a $CO_2$ added pressure of 40 psi (270 KPa) (total system pressure of 205 psia (1413 KPa)) every attempt (a total of six) to ignite the mixture failed to do so. The 270 KPa pressure caused by the $CO_2$ addition provided a $CO_2$ molar volume of about 20% in the bomb.

In another experiment, at an added pressure of 20 psi (138 KPa) (to a total system pressure of 185 psia (1275 KPa)) five out of nine attempts to ignite the mixture were successful. This added $CO_2$ pressure gave about 10 mol % $CO_2$ in the bomb.

In still another experiment, at 30 psi (207 KPa) added pressure (roughly 15 mol % $CO_2$), six out of seven attempts failed to ignite the mixture.

EXAMPLE 8

Ignition Test: Series TM 2

General Procedure

A mixture of carbon dioxide ($CO_2$) and tetrafluoroethylene (TFE) was made up by weight in a double-valved 0.5 liter stainless steel cylinder (mixing vessel). The $CO_2$ was taken from a supply container of liquified $CO_2$ containing a dip tube to deliver liquid. The mixing vessel contained a dip tube equipped with a fitted metal element at its tip (approximately 2.54 cm from the bottom of the cylinder) to help disperse the TFE. The mixing vessel was wrapped with heating tape, evacuated, pre-cooled under dry ice, and then mounted on a calibrated weighing scale. A specified amount of $CO_2$ liquid was added, followed by a specified amount of −20 C. TFE liquid, with the total estimated volume not to exceed approximately 85% of the volume of the cylinder. The cylinder was then removed from the scale and rocked between a horizontal and a tilted position to further mix the $CO_2$ and TFE. The cylinder was then mounted vertically over a previously evacuated 1.64 liter test vessel (bomb) with separate connections to the bomb from both the top and bottom valves of the mixing vessel. The mixing vessel was then insulated and its contents remotely drained into the test vessel. The mixing vessel and bomb were then heated to well above the liquid mixture's critical temperature forming a uniform single gas phase in both vessels.

Typical Loads

As an example of low-pressure loading, a 19.5 mol % $CO_2$ mixture in TFE was prepared using 15 grams $CO_2$ (0.34 mols) plus 140 grams TFE (1.40 mols) in the mixing vessel, which, upon connection to the bomb, reached a test pressure of 290 psia (1997 KPa) at 59° C. The composition of the top and bottom of the bomb by gas chromatographic analysis was 19.9 and 19.6 mol % $CO_2$ respectively.

As an example of high-pressure loading, a 30.6 mol % $CO_2$ mixture in TFE is prepared using 667 grams $CO_2$ (15.2 mols) plus 3442 grams TFE (34.4 mols) in a 1-gallon cylinder, which, upon connection to the bomb reached a test pressure of 1664 psia (11469 KPa) at 66° C. The composition of the top and bottom of the test vessel by gas chromatographic analysis was 29.9 and 29.5 mol % $CO_2$ respectively.

Explosion Testing

After reaching the test temperature, the mixing vessel was isolated by valves from the test bomb. The bomb was oriented in the horizontal plane, and was equipped with a 20-gauge Nichrome hot wire ignitor, 2.5 inches in length, placed at one end of the bomb, along its horizontal centerline. It was also equipped with a strain gage pressure transducer and a sheathed thermocouple, both connected to appropriate signal recording instrumentation.

The Nichrome wire ignitor was activated. If no significant reaction occurred, the power to the ignitor was increased until the wire fused at its melting point (1350 C.).

For both the low-pressure loading experiment at 20 mol % $CO_2$ at 1997 KPa at 59 C., and the high-pressure loading case at 30 mol % $CO_2$ at 11469 KPa at 66 C., no ignition of the mixtures was observed, i.e., no pressure rise on the gage attached to the bomb occurred.

What is claimed is:

1. A container of liquid mixture consisting essentially of tetrafluoroethylene and carbon dioxide under pressure.

2. The container of claim 1, wherein said liquid mixture fills less than the entire volume of said container to form a vapor space therein, said vapor space being filled with a mixture of tetrafluoroethylene and carbon dioxide vapor vaporized from said liquid mixture.

3. The container of claim 1, wherein said liquid mixture contains 1 to 99 mol % of said tetrafluoroethylene and 99 to 1 mol % of said carbon dioxide.

4. The container of claim 3, wherein the proportion of carbon dioxide in said liquid mixture is at least 20 mol %.

5. The container of claim 3, wherein the proportion of carbon dioxide in said liquid mixture is at least 60 mol %.

6. The container of claim 2 wherein the amount of carbon dioxide in said liquid mixture is sufficient to provide at least 30 mol % carbon dioxide in said vapor mixture over the temperature range of −50° to +55° C.

7. The container of claim 1 wherein its contents are at a temperature within the range of the critical temperature of said liquid mixture and 55° C.

8. The container of claim 7 wherein said pressure is at least 790 KPa.

9. In the process of transporting liquid tetrafluoroethylene in a container under pressure, the improvement consisting essentially of combining liquid carbon dioxide and said liquid tetrafluoroethylene, one with the other, said carbon dioxide being present in effective amount to prevent the tetrafluoroethylene vaporized from the resultant liquid mixture from exploding at temperatures up to 25° C.

10. In the process of claim 9, wherein the resultant vapor mixture of carbon dioxide and tetrafluoroethylene in said container will exhibit a change in vapor pressure of less than 10% after 50 wt % of said liquid has vaporized from the container.

11. In the process of claim 9 wherein the amount of carbon dioxide present is effective to prevent the tetrafluoroethylene vaporized from the resultant liquid mixture from exploding at temperatures up to +55° C.

12. A liquid mixture consisting essentially of tetrafluoroethylene and carbon dioxide.

13. The liquid mixture of claim 12 as an azeotrope-like composition consisting essentially of about 30 to 99 mol % carbon dioxide and 70 to 1 mol % tetrafluoroethylene, said composition having a boiling point of +25° C. when the pressure is adjusted to about 4000 to 6600 KPa.

14. The liquid mixture of claim 12 as an azeotrope consisting essentially of about 96 mol % carbon dioxide and 4 mol % tetrafluoroethylene, said composition having a boiling point of about ±35° C. when the pressure is adjusted to about 1205 KPa.

15. The container of claim 2 wherein said liquid mixture fills from 50 to 90% of said entire volume.

16. In the process of claim 9 wherein said liquid mixture fills from 50 to 90% of the entire volume of said container.

17. In the process of claim 9 wherein the container in which said tetrafluoroethylene and carbon dioxide are combined is also transported.

* * * * *

UNITED STATES PATENT AND TRADEMARK OFFICE
CERTIFICATE OF CORRECTION

PATENT NO. : 5,345,013
DATED : Sep. 6, 1994
INVENTOR(S) : Van Bramer et al.

It is certified that error appears in the above-identified patent and that said Letters Patent is hereby corrected as shown below:

Claim 9, column 12, line 20: "25°C" should be -- +25°C --.
Claim 14, column 12, line 41: "±35°C" should be -- -35°C --.

Signed and Sealed this

Twenty-seventh Day of December, 1994

Attest:

BRUCE LEHMAN

*Attesting Officer*      *Commissioner of Patents and Trademarks*